US009452080B2

(12) United States Patent
Holzbauer et al.

(10) Patent No.: US 9,452,080 B2
(45) Date of Patent: *Sep. 27, 2016

(54) FECAL DRAINAGE SYSTEM WITH MULTI-LAYER ODOR BARRIER CATHETER TUBE (71) Applicant: Hollister Incorporated, Libertyville, IL (US)

(72) Inventors: Todd J. Holzbauer, Hockessin (DE); Adel Sadik, Fox River Grove, IL (US); Moh-Ching Oliver Chang, Lake in the Hills, IL (US); George J. Cisko, Jr., Spring Grove, IL (US)

(73) Assignee: HOLLISTER INCORPORATED, Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/599,980

(22) Filed: Jan. 19, 2015

(65) Prior Publication Data
US 2015/0133880 A1 May 14, 2015

Related U.S. Application Data (63) Continuation of application No. 13/359,968, filed on Jan. 27, 2012, now Pat. No. 8,936,583, which is a continuation-in-part of application No. 12/238,584, filed on Sep. 26, 2008, now Pat. No. 8,734,411.

(60) Provisional application No. 60/976,214, filed on Sep. 28, 2007.

(51) Int. Cl.
*A61F 5/441* (2006.01)
*A61F 5/44* (2006.01)
*A61M 25/00* (2006.01)

(52) U.S. Cl.
CPC .......... *A61F 5/441* (2013.01); *A61M 25/0045* (2013.01); *A61F 5/44* (2013.01); *A61M 2202/068* (2013.01)

(58) Field of Classification Search
CPC .......... A61M 1/008; A61M 2202/068; A61M 25/0045
See application file for complete search history.

(56) References Cited

U.S. PATENT DOCUMENTS 2,800,145 A 7/1957 Peierls, et al.
3,561,493 A 2/1971 Maillard et al.
(Continued)

FOREIGN PATENT DOCUMENTS

EP 0366802 5/1990
EP 0469926 2/1992
(Continued)

OTHER PUBLICATIONS

International Search Report of PCT/US2008/077796, mailed Dec. 23, 2008, 5 pages.
(Continued)

*Primary Examiner* — Susan Su
(74) *Attorney, Agent, or Firm* — Lempia Summerfield Katz LLC (57) ABSTRACT A fecal drainage system includes a collection bag and a catheter tube connectable to the collection bag. The catheter tube is a multi-layer odor barrier structure. The layers of the catheter tube include one or more thermoplastic elastomer layers and one or more odor barrier layers. For example, the catheter tube may comprise an inner thermoplastic elastomer (TPE) layer, an intermediate odor barrier film layer, and an outer TPE layer. Alternately, the multi-layer catheter tube includes an inner TPE layer sandwiched between outer layers of odor barrier film material.

18 Claims, 7 Drawing Sheets

(56) References Cited

U.S. PATENT DOCUMENTS

| | | | |
|---|---|---|---|
| 4,312,693 A | 1/1982 | Salensky et al. |
| 4,376,799 A | 3/1983 | Tusim |
| 4,445,898 A | 5/1984 | Jensen |
| 4,627,844 A | 12/1986 | Schmitt |
| 4,650,817 A | 3/1987 | Allen, Jr. et al. |
| 4,687,711 A | 8/1987 | Vietto et al. |
| 4,721,508 A | 1/1988 | Burton |
| 4,778,553 A | 10/1988 | Wood |
| 4,906,495 A | 3/1990 | Martini et al. |
| 5,084,315 A | 1/1992 | Karimi et al. |
| 5,171,305 A | 12/1992 | Schickling et al. |
| 5,261,898 A | 11/1993 | Polin et al. |
| 5,277,753 A | 1/1994 | Kelley et al. |
| 5,290,613 A | 3/1994 | Shuetz et al. |
| 5,356,400 A | 10/1994 | Temple |
| 5,356,709 A | 10/1994 | Woo et al. |
| 5,364,662 A | 11/1994 | Domenico et al. |
| 5,386,817 A | 2/1995 | Jones |
| 5,407,713 A | 4/1995 | Wilfong et al. |
| 5,439,454 A | 8/1995 | Lo et al. |
| 5,439,545 A | 8/1995 | Nakanishi et al. |
| 5,466,424 A | 11/1995 | Kusano et al. |
| 5,468,526 A | 11/1995 | Allen et al. |
| 5,470,624 A | 11/1995 | Oreglia et al. |
| 5,480,377 A | 1/1996 | Cartmell et al. |
| 5,488,975 A | 2/1996 | Chiles et al. |
| 5,496,295 A | 3/1996 | Wilfong et al. |
| 5,529,820 A | 6/1996 | Nomi et al. |
| 5,567,488 A | 10/1996 | Allen et al. |
| 5,567,489 A | 10/1996 | Allen et al. |
| 5,569,216 A | 10/1996 | Kim |
| 5,643,375 A | 7/1997 | Wilfong et al. |
| 5,681,627 A | 10/1997 | Mueller |
| 5,686,173 A | 11/1997 | Fujii et al. |
| 5,730,919 A | 3/1998 | Wilfong et al. |
| 5,738,923 A | 4/1998 | Ko et al. |
| 5,759,173 A | 6/1998 | Preissman et al. |
| 5,908,656 A | 6/1999 | Ishikawa et al. |
| 5,928,744 A | 7/1999 | Heilmann et al. |
| 5,932,307 A | 8/1999 | Ryan et al. |
| 5,983,604 A | 11/1999 | Wilfong et al. |
| 5,986,003 A | 11/1999 | Lee et al. |
| 6,050,982 A | 4/2000 | Wheeler |
| 6,057,414 A | 5/2000 | Razavi |
| 6,136,394 A | 10/2000 | Karsten |
| 6,143,383 A | 11/2000 | Giori |
| 6,165,166 A | 12/2000 | Samuelson et al. |
| 6,217,547 B1 | 4/2001 | Lee |
| 6,258,423 B1 | 7/2001 | Giori |
| 6,286,555 B1 | 9/2001 | Pauker et al. |
| 6,299,596 B1 | 10/2001 | Ding |
| 6,406,767 B1 | 6/2002 | Mueller |
| 6,431,219 B1 | 8/2002 | Redler et al. |
| 6,447,835 B1 | 9/2002 | Wang et al. |
| 6,455,161 B1 | 9/2002 | Regnier et al. |
| 6,620,474 B1 | 9/2003 | Regnier et al. |
| 6,663,614 B1 | 12/2003 | Carter |
| 6,770,342 B2 | 8/2004 | Buongiorno |
| 6,776,195 B2 | 8/2004 | Blasko et al. |
| 6,869,653 B2 | 3/2005 | Ling et al. |
| 6,945,970 B2 | 9/2005 | Pepin |
| 6,964,816 B2 | 11/2005 | Schell et al. |
| 6,977,105 B1 | 12/2005 | Fujieda et al. |
| 7,015,284 B2 | 3/2006 | Ajbani et al. |
| 7,090,664 B2 | 8/2006 | Holter |
| 7,100,767 B2 | 9/2006 | Chomik et al. |
| 7,112,298 B2 | 9/2006 | Kampa et al. |
| 7,147,627 B2 | 12/2006 | Kim et al. |
| 7,270,860 B2 | 9/2007 | Giori |
| 7,361,170 B2 | 4/2008 | Williams et al. |
| 7,396,582 B2 | 7/2008 | Claude et al. |
| 7,481,804 B2 | 1/2009 | Devens, Jr. |
| 7,550,185 B2 | 6/2009 | Ling et al. |
| 7,628,784 B2 | 12/2009 | Diaz et al. |
| 7,647,949 B2 | 1/2010 | Donohue et al. |
| 7,722,583 B2 | 5/2010 | Kim et al. |
| 8,323,254 B2 | 12/2012 | Tsai et al. |
| 8,399,077 B1 | 3/2013 | Bekele |
| 2002/0016607 A1 | 2/2002 | Bonadio et al. |
| 2003/0064182 A1 | 4/2003 | Giori |
| 2003/0131569 A1 | 7/2003 | Chomik et al. |
| 2003/0218022 A1 | 11/2003 | Chomik et al. |
| 2004/0134555 A1 | 7/2004 | Powell et al. |
| 2004/0175525 A1 | 9/2004 | Willard et al. |
| 2004/0228992 A1 | 11/2004 | Giori |
| 2005/0038374 A1 | 2/2005 | Williams, Jr. et al. |
| 2005/0054996 A1 | 3/2005 | Gregory |
| 2005/0075616 A1 | 4/2005 | Holter |
| 2005/0182387 A1 | 8/2005 | Webler |
| 2005/0273064 A1 | 12/2005 | Dircks et al. |
| 2006/0147698 A1 | 7/2006 | Carroll et al. |
| 2006/0249418 A1 | 11/2006 | Chomik et al. |
| 2006/0253102 A1 | 11/2006 | Nance et al. |
| 2007/0043333 A1 | 2/2007 | Kampa et al. |
| 2007/0051418 A1 | 3/2007 | Rowles et al. |
| 2008/0032110 A1 | 2/2008 | Wood et al. |
| 2008/0103463 A1 | 5/2008 | Tsai et al. |
| 2008/0262447 A2 | 10/2008 | Martino et al. |
| 2009/0048537 A1 | 2/2009 | Lydon et al. |
| 2009/0088711 A1 | 4/2009 | Shelley et al. |
| 2009/0169788 A1 | 7/2009 | Pandey et al. |
| 2009/0202759 A1 | 8/2009 | O'Brien et al. |
| 2009/0240235 A1 | 9/2009 | Murata |
| 2010/0055357 A1 | 3/2010 | Ciccarello |
| 2010/0055367 A1 | 3/2010 | Ohigawa |
| 2010/0174252 A1 | 7/2010 | Tanghoej et al. |
| 2010/0274201 A1 | 10/2010 | Feeley et al. |

FOREIGN PATENT DOCUMENTS

| | | |
|---|---|---|
| EP | 0575798 | 12/1993 |
| EP | 0615832 | 9/1994 |
| JP | 54074514 | 6/1979 |
| JP | 3041176 | 2/1991 |
| JP | 3050262 | 3/1991 |
| JP | 4100857 | 4/1992 |
| JP | 2001227682 | 8/2001 |
| WO | WO9923158 | 5/1999 |
| WO | WO2008052018 A2 | 5/2008 |

OTHER PUBLICATIONS

Lai et al., Surface Modification of Silicone Rubber by Gas Plasma Treatment, J. Adhesion Sci. Technol., 10 (3):231-243 (1996).

Written Opinion of PCT/US2008/077796, mailed Dec. 23, 2008, 8 pages.

FECAL DRAINAGE SYSTEM WITH MULTI-LAYER ODOR BARRIER CATHETER TUBE

RELATED APPLICATION DATA

This application is a continuation under 37 C.F.R. §1.53 (b) and 35 U.S.C. §120 of U.S. patent application Ser. No. 13/359,968 filed on Jan. 27, 2012 which is a Continuation-in-Part of U.S. patent application Ser. No. 12/238,584, filed Sep. 26, 2008, which claimed priority benefit of the filing date of U.S. Provisional Application No. 60/976,214, filed Sep. 28, 2007. The entire contents of each of the aforementioned U.S. patent applications are hereby incorporated herein by reference.

FIELD OF THE DISCLOSURE

This disclosure is generally directed to medical tubing and, more specifically, to multi-layered tubing having odor barrier properties suitable for use as catheter tubing for fecal drainage systems, and a combination odor barrier tube and odor barrier collection bag.

BACKGROUND

Catheter tubes for fecal drainage systems are designed to facilitate flow of fecal matter, with the fecal matter typically draining into a collection bag. A catheter tube can include a lubricious coating on an interior of the tube to facilitate movement of fecal matter. By providing a multi-layer catheter tube with at least one odor barrier layer, the catheter tube can reduce or eliminate exposure of the patient, caregivers, and other persons in the vicinity of the patient to unpleasant odors. Also, because it is desirable for rectal catheters to be retained in the rectal cavity for extended durations, it has been found beneficial to provide rectal catheters with a transsphincteric region that is collapsible in response to contraction of the patient's anal sphincter muscles, as described in U.S. Pat. Nos. 7,147,627 and 7,722,583. Silicone is a preferred material for the transsphincteric region.

In providing a catheter tube extending between the transsphincteric region and a collection bag, not only is it desirable to prevent odor transmission, but it is also desirable to provide resistance to kinking of the catheter tube, because kinking can obstruct the flow of fecal matter therethrough. Fecal drainage systems are frequently employed in combination with enema, lavage, or other irrigation techniques to loosen stool in the rectum of a patient. As a result, water or other liquid is likely to travel through the catheter tube with fecal matter. While such liquid reduces the need to provide a lubricious surface on the interior of the catheter tube, it is desirable for the exterior of the catheter tube to be lubricious, as this facilitates milking the catheter tube to move waste material along the length of the catheter tube.

SUMMARY

In preferred embodiments of the present disclosure, the catheter tubing for a fecal drainage system is made of at least two layers of different materials. The layers are preferably co-extruded, or one layer may be extruded and one or more layers may be subsequently applied by extrusion over the first layer. Alternatively, the layers may be formed as a generally flat laminate sheet that is rolled into a tubular shape, then sealed along a seam, for example using sealing technology such as heat sealing, RF sealing, adhesive sealing, or ultrasonic welding. In order to increase the catheter tube's durability, a semi-rigid mesh or scrim material may be included as at least one of the layers of the flat laminate sheet that is rolled into a cylinder.

Another desirable feature of a catheter tube for a fecal drainage system is minimal wall thickness. The multi-layer odor barrier catheter tube of the present disclosure can be manufactured with a total wall thickness in the range of about 10 mil to about 60 mil, and preferably with a total wall thickness of 25 mil. The total wall thickness of 25 mil is preferable for all embodiments of the catheter tube described herein, regardless of the arrangement of catheter tube layers and the total number of layers.

The odor barrier layer or layers may be a resin, preferably a polyamide, and most preferably nylon 669 or nylon 669 blended with reactive rubber. In one embodiment, an odor barrier layer is sandwiched between two layers of thermoplastic elastomer (TPE). In another embodiment, a plurality of odor barrier layers may be alternately sandwiched between a plurality of layers of TPE. In yet another embodiment, the odor barrier layer is an intermediate layer of a plurality of layers of the catheter tube.

To prevent kinking of the catheter tube, which may adversely impact the catheter tube's function, a low compression set thermoplastic elastomer is preferably used for each of catheter tube's TPE layers. The inner TPE layer, which is thicker than the one or more outer TPE layers and which makes up the bulk of the overall thickness of the catheter tube, preferably has a thickness in a range of 12 mil to 24 mil, and most preferably has a thickness of 18 mil. The outer TPE layer preferably has a thickness in the range of 5 mil to 8 mil, and most preferably has a thickness of 6 mil. The outer TPE layer may be formulated so as to exhibit high lubricity, i.e. a low coefficient of friction. High lubricity of the outer TPE layer facilitates relative movement of a latex- or non-latex-gloved hand along the exterior of the catheter tube when milking contents of the catheter tube toward a collection bag in fluid communication with the interior of the catheter tube. While lubricity of the inner TPE layer may also be desirable to promote or facilitate flow of fecal matter through the catheter tube, it is found that there is typically sufficient liquid content with the waste matter draining through the catheter tube such that the inner TPE layer need not exhibit as high a lubricity as the outer TPE layer.

The odor barrier layer of the catheter tube of this embodiment preferably has a thickness of 3 mil or less, most preferably 1 mil, and the thickness of the odor barrier is preferably less than 30% of the total tube wall thickness.

In an embodiment of the present disclosure, one or more layers of TPE may be sandwiched between two or more layers of odor barrier material such as nylon PA 669 or nylon PA 669 blended with a reactive rubber. In another embodiment, a TPE layer is an intermediate layer of a plurality of layers of the catheter tube.

In this embodiment, the inner TPE layer, which also makes up the bulk of the overall thickness of the catheter tube, preferably has a thickness in a range of 10 mil to 60 mil, and most preferably has a thickness of 24 mil. Each of the outer odor barrier layers preferably has a thickness in the range of 0.25 mil to 1.5 mil, and most preferably has a thickness of 0.5 mil, such that the overall thickness of the catheter tube is, most preferably, 25 mil. While lubricity of the inner nylon layer may be desirable to promote or facilitate flow of fecal matter through the catheter tube, as before, there may be sufficient liquid content with the waste matter draining through the catheter tube of this embodiment such that the inner nylon layer need not exhibit as high a lubricity as the outer nylon layer.

A beneficial aspect of the catheter tube of embodiments of this disclosure is the ability of the catheter tube to block unpleasant odors. However, if the collection bag into which the catheter tube drains lacks odor barrier properties, unpleasant odors can escape the collection bag, thereby negating the odor barrier benefits achieved by the odor barrier catheter tube of this disclosure. It is therefore preferable that the odor barrier tube to drain into a collection bag that itself has odor barrier walls.

DETAILED DESCRIPTION OF THE DISCLOSURE

Figure 1:
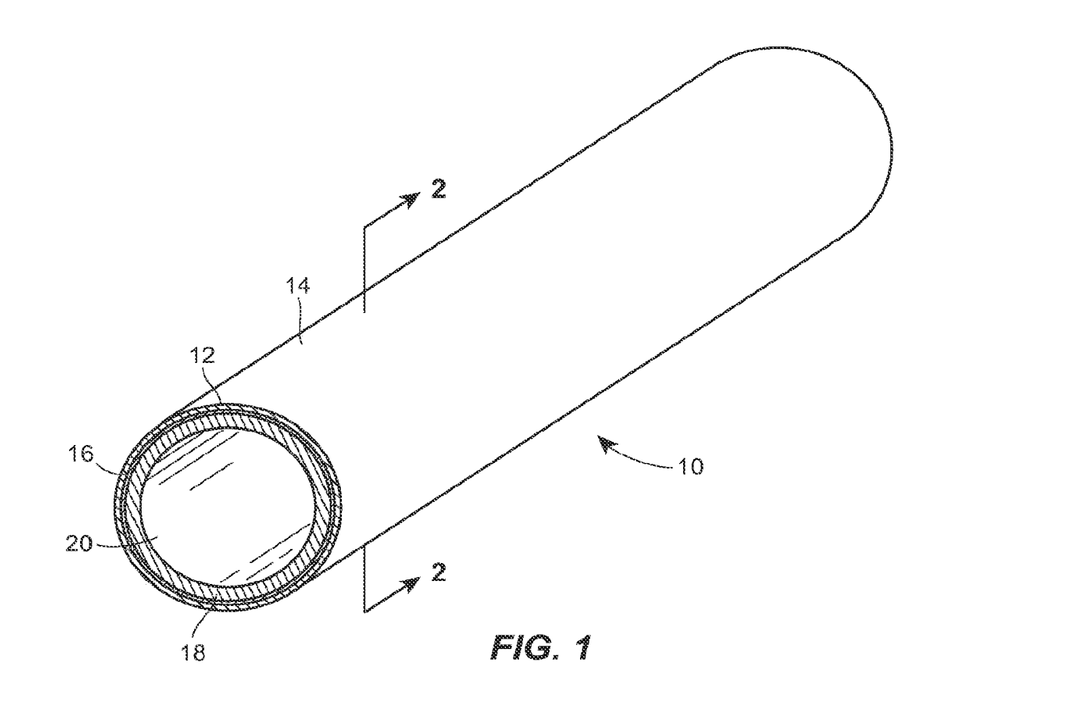
FIG. 1 is a perspective view of a first embodiment of a multi-layer odor barrier catheter tube of the present disclosure.
Figure 2:
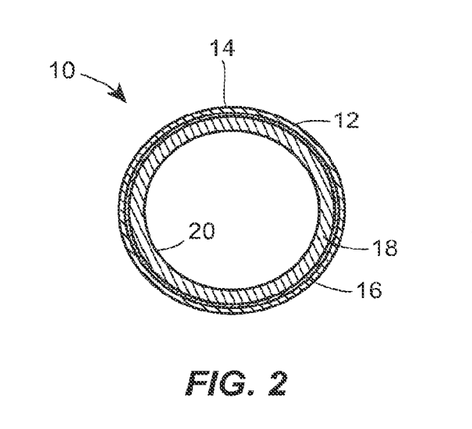
FIG. 2 is an axial cross-sectional view, taken along lines 2-2 of FIG. 1.

With reference to FIGS. 1-2, in a first embodiment of a multi-layer odor barrier catheter tube 10 of the present disclosure, the catheter tube 10 is connectable at a first end to a patient-proximal internal section, and/or a trans-anal section of a rectal catheter (not shown). The catheter tube 10 is also connectable at a second end to a waste collection bag or to a disposal receptacle (e.g., a bedpan or toilet (not shown)). At least one layer of the multi-layer catheter tube 10 is constructed of a material resistant to transmission of fecal and flatus gasses. A suitable material is nylon, and preferably low-modulus nylon such as nylon PA 669. EMS-Grivory's GRILON® BM 13 SBG is a suitable low-modulus nylon, with its modulus of approximately 43 ksi compared to typical nylon PA6 with a modulus of about 100 ksi. Another suitable material is nylon PA669 blended with reactive rubber to reduce the modulus and set of the blend. For example, nylon PA669 could be blended with Kraton® FG1924, LOTADER® 4720, or DuPont Fusabond® 493. A suitable blend would be, for example, 75% EMS-Grivory GRILON® BM 13 SBG compounded with 25% LOTADER® 4720. In addition, one or more lubricants may be added to the blend. These lubricants may include, for example, an amide wax (e.g., erucamide, oleamide, stearyl erucamide), an ester wax (e.g., esters of montanic acids), or silicon oil preferably used at 0.05% to 0.5% loading to generate a low surface coefficient of friction.

A first layer 12 of the catheter tube 10 defines the external surface 14 of the catheter tube 10. The first layer 12 is preferably comprised of one or more materials that possess a relatively low coefficient of friction, most preferably less than 0.5, so as to reduce drag of the catheter tube 10 against a patient's skin and against any items surrounding the patient, such as a hospital gown, bed sheets, or a chair. The low coefficient of friction of the external surface 14 of the catheter tube 10 also facilitates "milking" the fecal matter down the length of the catheter tube 10.

The material or materials defining the first layer 12 of the catheter tube 10 include a thermoplastic elastomer (TPE), preferably having a thickness in the range of 4 mil to 8 mil, and most preferably a thickness of 6 mil. TPE exhibits adequate lubricity, particularly TPE having a Shore A hardness of approximately 60. The external surface 14 of the first layer 12 is preferably a surface that will receive inks such as permanent or semi-permanent markers and retain such markings thereon without smudging or wiping off. This will facilitate receiving instructions, patient data, collection bag change data, dates of indwell or intended removal of the catheter tube, and other such indicia.

An intermediate layer 16 of the catheter tube 10 of an embodiment of the present disclosure is an odor barrier film layer, preferably a polyamide, and most preferably nylon 669.

An inner layer 18 of the multi-layer catheter tube 10 of an embodiment of the present disclosure preferably comprises TPE having a thickness in a range of 12 mil to 24 mil. The inner layer 18 most preferably has a thickness of 18 mil. The inner layer 18 is preferably the thickest layer of the catheter tube 10 and is formulated for low compression-set, with high elasticity, as this is found to render the catheter tube 10 more resistant to developing kinks, such as when folded in packaging material.

Figure 3:
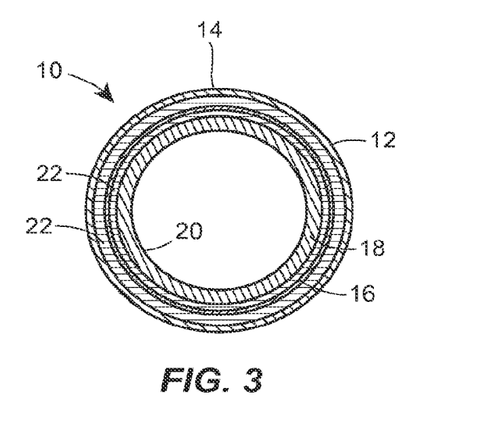
FIG. 3 is an axial cross-sectional view, similar to FIG. 2, of a second embodiment of a multi-layer odor barrier catheter tube of the present disclosure, wherein tie layers are provided between the first and second layers, and between the second and third layers.

Depending on the compatibility of the materials of adjacent layers of the multi-layered catheter tube 10, as shown in FIG. 3, a tie layer 22, such as DuPont Bynel®, may be employed between adjacent layers to improve adhesion of the adjacent layers to one another. However, in a preferred embodiment of the present disclosure, the materials of adjacent layers of the multi-layer catheter tube are compatible and do not require a tie layer be employed between adjacent layers to improve adhesion of the adjacent layers to one another.

The multi-layer catheter tube 10 of the first embodiment of the present disclosure may be manufactured by co-extrusion. In order to maximize tube softness and flexibility, it is desirable that a catheter tube 10 of some embodiments of the present disclosure include a single, thin odor barrier layer, preferably 1 mil. In embodiments of the catheter tube 10 with more than one odor barrier layer, the odor barrier layers preferably have a thickness of 0.25 mil to 1.5 mil.

Figure 4:
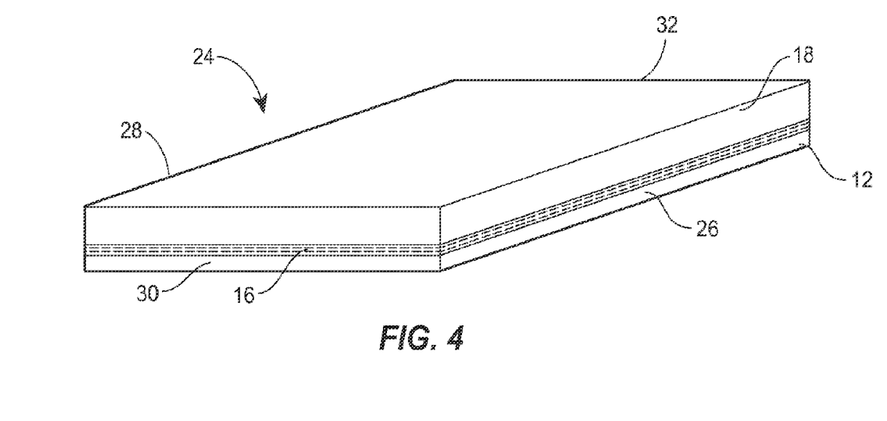
FIG. 4 is a perspective view of a heat-laminated film employed in a method of manufacture of a multi-layer odor barrier catheter tube of the present disclosure.
Figure 5:
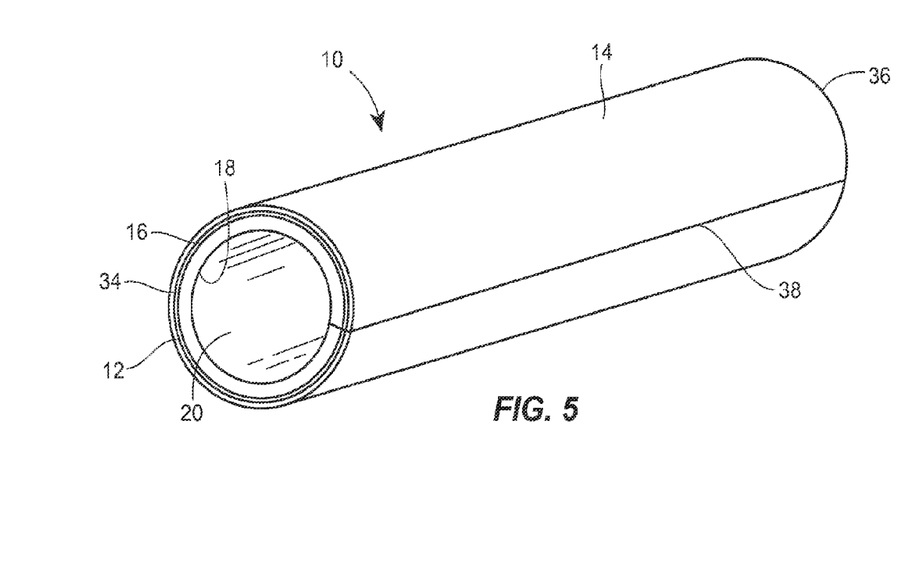
FIG. 5 is a perspective view of the heat-laminated film of FIG. 4, rolled into a cylindrical shape and sealed along a seam.

Turning to FIGS. 4-5, as an alternative to co-extrusion, the layers of the catheter tube 10 may be formed into a flat or substantially flat heat-laminated film 24 and then rolled into a cylinder. For example, in one embodiment of the present disclosure as illustrated in FIGS. 4-5, two parallel edges 26, 28 are rolled toward one another, brought into register with one another, and sealed to one another, such as by heat sealing, RF sealing, adhesive sealing, or ultrasonic welding, to form a cylinder, with the first layer 12 of the film 24 defining an external surface 14 of the cylinder and the third layer 18 defining an internal surface 20 of the cylinder. A leading end 30 and a trailing end 32 of the heat-laminated film 24 are left open, forming first and second ends 34, 36 of the catheter tube 10. Optionally, tie layers (represented by broken lines in FIG. 4) may be provided to enhance bonding between the inner layer 18 and intermediate odor barrier layer 16, and/or between the intermediate layer 16 and the outer layer 12. The first, second, and intermediate layers 12, 18, 16 of the catheter tube 10 are preferably clear or translucent. The sealed edge or seam 38 may be visible and can advantageously provide a medical caregiver with a visible indicator of any kinking or twisting of the catheter tube.

The total cumulative wall thickness of the multi-layer catheter tube 10 is preferably in the range of about 10 mil to about 40 mil, and more preferably in a range of about 25 mil to about 35 mil, with the thickness of the odor barrier layer preferably making up less than about 30% of the total wall thickness of the catheter tube 10.

Adjustments may be made to process conditions under which the layers of the multi-layer catheter tube of the present disclosure are co-extruded or heat laminated to reduce the coefficient of friction of one or more of the layers.

Figure 6:
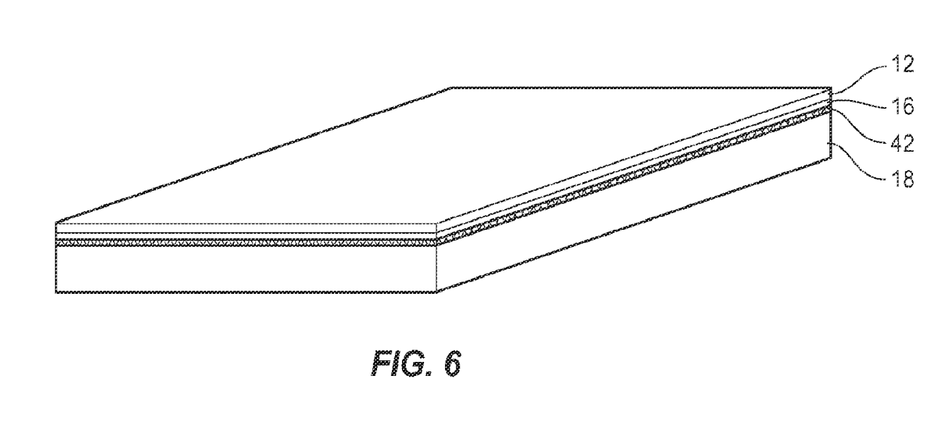
FIG. 6 is a perspective view of a heat-laminated film similar to that of FIG. 4, and including a flexible scrim layer.
Figure 7:
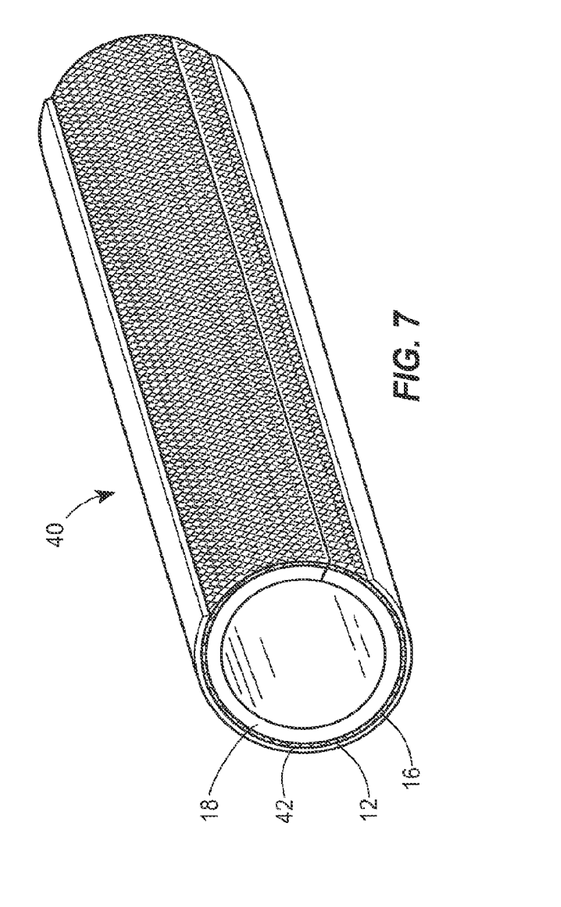
FIG. 7 is a perspective view of the heat-laminated film of FIG. 6, rolled into a cylindrical shape and sealed along a seam.

In another embodiment, shown in FIGS. 6-7, in order to provide reinforcement and avoid kinking or twisting of a catheter tube 40, a mesh or flexible scrim layer 42 may be included as an additional layer intermediate the first layer 12 and intermediate layer 18 of the multi-layer catheter tube 40. The scrim layer 42, if provided, can serve to provide the catheter tube 40 with shape memory, permitting the catheter tube 40 to collapse and recover to its cylindrical shape without any permanent deformation. Materials other than a scrim layer 42 may be used instead of or in addition to the scrim layer 42 to enhance structural integrity of the catheter tube 40, such as polymeric materials.

The material(s) forming the internal and/or external surfaces of the multi-layer catheter tube of the present disclosure preferably facilitate attachment and assembly of the catheter tube to peripheral components of fecal drainage and management systems, such as the Bowel Management System available from Hollister Incorporated of Libertyville, Ill. As such systems are intended for long-duration use, on the order of about twenty-nine days, it is advantageous to employ materials that will easily form a reliable bond, by adhesive and/or heat, between the catheter tube 10 and the peripheral components, such as internal or external silicone balloons, catheter connections (e.g., a collection bag or a catheter tube extension), plastic or metal ports (e.g., ports for providing endoscope access or for sampling fecal matter directly from the catheter tube) for the entire duration of use of the catheter tube 10.

As noted above, the advantages achieved by the odor barrier properties of the catheter tubes of the present disclosure would be negated, or significantly diminished, if fecal or flatus gasses could be transmitted through one or more walls of a collection bag 44 (see FIG. 8) to which the catheter tube 10 is connected. It is therefore desirable to use the multi-layer odor barrier catheter tube 10 in combination with a collection bag 44 having odor barrier walls. For example, each of the walls of the collection bag may include a barrier layer film such as the one disclosed in U.S. Pat. No. 7,270,860.

Figure 8:
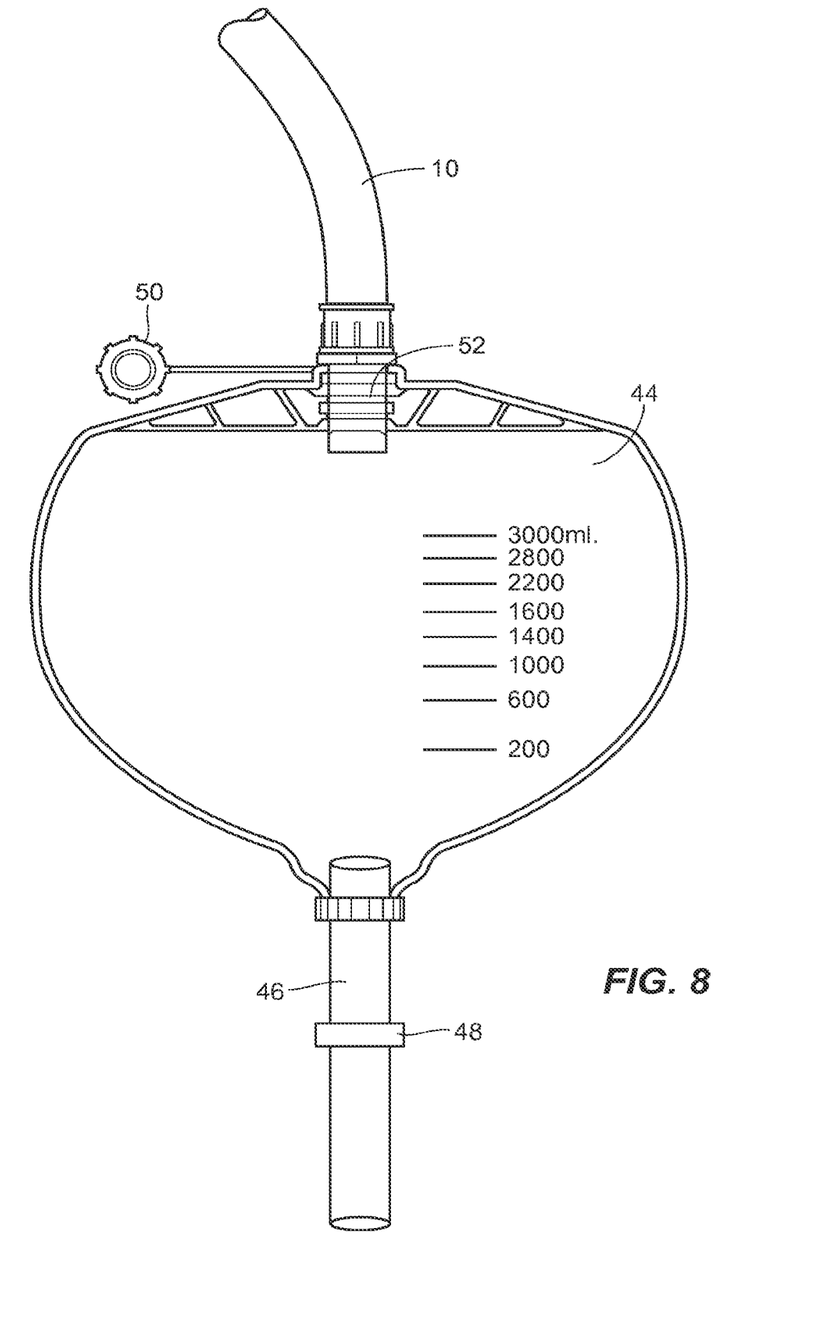
FIG. 8 is a front view of a combination of a multi-layer odor barrier catheter tube of the present disclosure in combination with a drainable collection bag having odor barrier walls.
Figure 9:
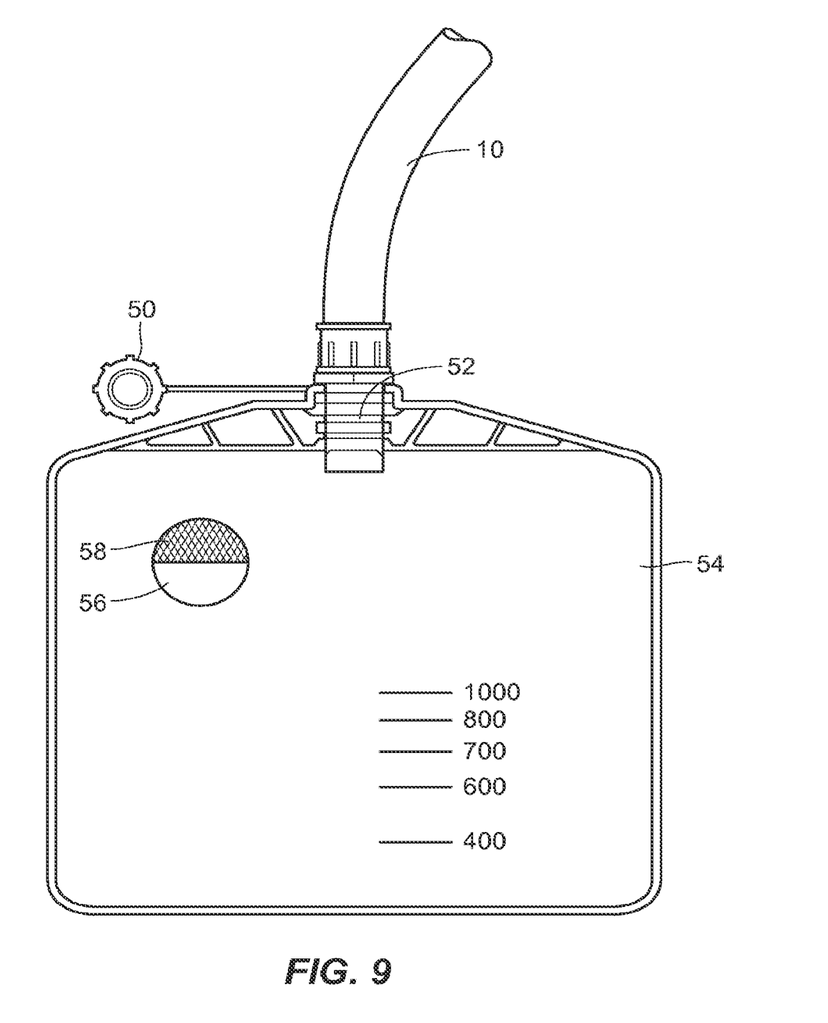
FIG. 9 is a front perspective view of a combination of a multi-layer odor barrier catheter tube of the present disclosure in combination with a closed, single-use collection bag having odor barrier walls.

Turning to FIG. 8, the odor barrier collection bag may be a drainable collection bag 44, having a drainage tube 46 with a drainage tube stopper 48 and a cap 50 for capping a catheter tube connection port 52. Alternately, as illustrated in FIG. 9, the odor barrier collection bag may be a so-called "closed" collection bag 54. A closed collection bag 54 is intended for single use, and preferably includes an integral vent 56 with a deodorizing filter 58.

Figure 10:
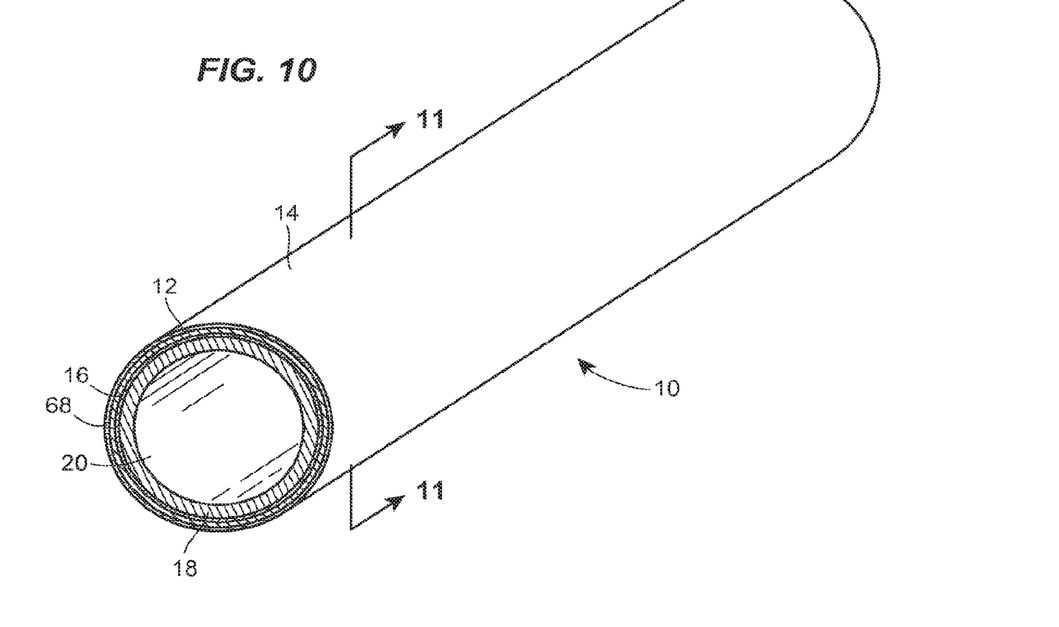
FIG. 10 is a perspective view of a third embodiment of a multi-layer odor barrier catheter tube of the present disclosure, including an outermost ethylene methyl acrylate (EMA) film surrounding an outer thermoplastic elastomer layer, the EMA film serving as a silicone bonding substrate.
Figure 11:
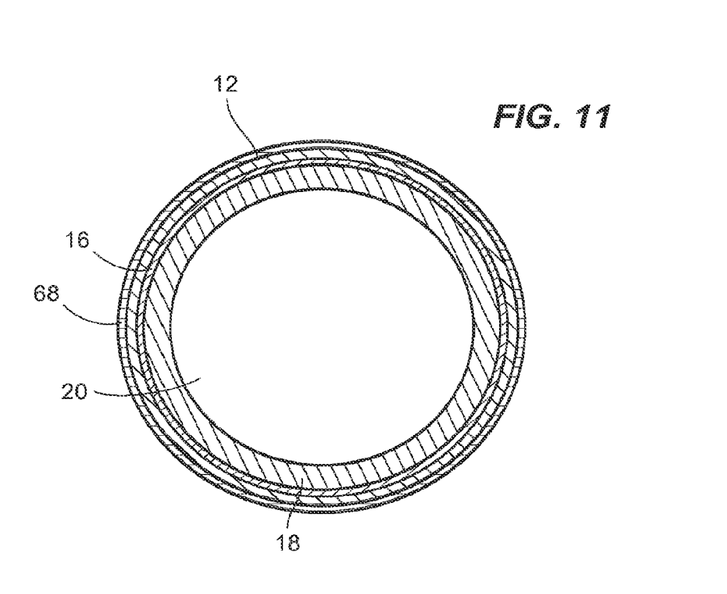
FIG. 11 is a cross-sectional view, taken along lines 11-11 of FIG. 10.

Turning to FIGS. 10 and 11, an alternate embodiment of a catheter tube is illustrated in which the outer TPE layer 12 of the catheter tube 10 has an ethylene methyl acrylate (EMA) film 68 bonded, such as by heat sealing, to at least the portion of the exterior thereof that is received in the silicone transsphincteric region 60. EMA film 68 bonds to silicone more readily than TPE. EMA film also exhibits high lubricity, thereby eliminating the need to formulate the outer TPE layer 12 in a manner that increases that layer's lubricity, or eliminating the need to add a lubricious coating, such as Parylene, to the exterior of the catheter tube 10.

Figure 12:
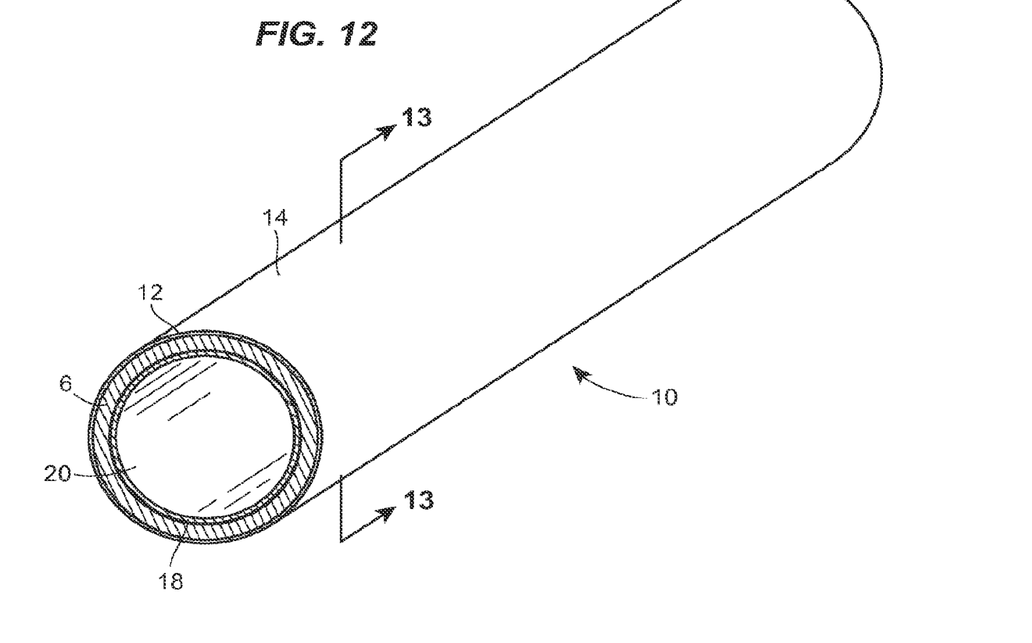
FIG. 12 is a perspective view of another embodiment of a multi-layer odor barrier catheter tube of the present disclosure, wherein the interior and exterior layers comprise an odor barrier material.

Turning to FIG. 12, in another embodiment of the present disclosure, an intermediate layer 16 comprising TPE may be sandwiched between a first layer 12 and an inner layer 18, both comprising an odor barrier material such as nylon PA 669 or nylon PA 669 blended with a reactive rubber. A beneficial aspect of this embodiment is that by sandwiching the intermediate layer 16 of TPE between the odor barrier layers 12, 13, difficulties of bonding TPE to silicone device components to which the multi-layer tubing 10 is attached may be avoided due to the compatibility of the nylon odor barrier material and silicone.

Figure 13:
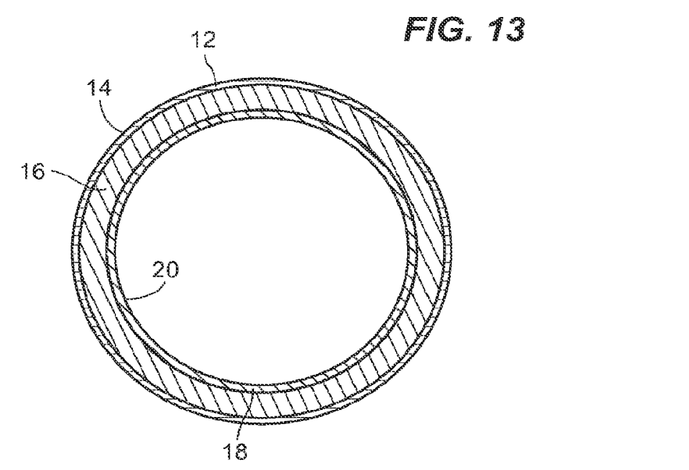
FIG. 13 is a cross-sectional view, taken along lines 13-13 of FIG. 12.

The TPE layer 16, which makes up the bulk of the overall thickness of the catheter tube 10 of this embodiment, preferably has a thickness in a range of 20 mil to 40 mil, and most preferably has a thickness of 24 mil. Each of the outer odor barrier layers 12, 18 preferably has a thickness in the range of 0.25 mil to 1.5 mil, and most preferably has a thickness of 0.5 mil, such that the overall thickness of the catheter tube is, most preferably, 25 mil. Furthermore, while lubricity of the inner nylon layer 18 may be desirable to promote or facilitate flow of fecal matter through the catheter tube 10, there may be sufficient liquid content with the waste matter draining through the catheter tube 10 of this embodiment such that the inner nylon layer 18 need not exhibit as high a lubricity as the outer nylon layer 12. In another embodiment of the present disclosure, the inner layer may be hydrophobic.

In each of the foregoing embodiments of the present disclosure, the TPE material may include or may be substituted by thermoplastic polyurethane (TPU), styrene-butadiene copolymer (SBC), thermoplastic vulcanisate (TPV), ethylene propylene diene monomer (EPDM), or any other suitable copolymer or blend.

While certain embodiments of multi-layer odor barrier catheter tubes, combinations of multi-layer odor barrier catheter tubes and odor barrier collection bags, and methods of manufacturing multi-layer odor barrier catheter tubes are disclosed herein, the appended claims are not intended to be limited thereto. Variations can be made to the disclosed embodiments that are still within the scope of the appended claims, literally or under the doctrine of equivalents.

What is claimed is:

1. A fecal drainage system comprising:
   a collection bag; and
   a catheter tube connectable to the collection bag, the catheter tube having a first layer including a thermoplastic elastomer, a second layer including a thermoplastic elastomer, and a film layer intermediate the first layer and the second layer, the film layer including an odor barrier material and comprising nylon 669.

2. The fecal drainage system of claim 1, wherein the first layer of the catheter tube defines an internal surface of the catheter tube and is the thickest layer of the catheter tube.

3. The fecal drainage system of claim 2, wherein the film layer of the catheter tube that is intermediate the first layer and the second layer is the thinnest layer of the catheter tube.

4. The fecal drainage system of claim 1, wherein the nylon 669 is blended with a reactive rubber.

5. The fecal drainage system of claim 4, wherein the nylon 669 blended with a reactive rubber further comprises one or more lubricants.

6. The fecal drainage system of claim 1, wherein the catheter tube further comprises a fourth layer bonded about at least a portion of an exterior of the second layer, the fourth layer including an ethylene methyl acrylate (EMA) film.

7. The fecal drainage system of claim 1, wherein the collection bag has one or more walls having odor barrier properties.

8. The fecal drainage system of claim 1, further comprising a one or more additional layers of the catheter tube that are intermediate the first layer and the second layer in addition to the film layer.

9. A fecal drainage system comprising:
   a collection bag; and
   a catheter tube connectable to the collection bag, the catheter tube having a first layer including an odor barrier material, a second layer including an odor barrier material, and a third layer intermediate the first layer and the second layer, the third layer including a thermoplastic elastomer.

10. The fecal drainage system of claim 9, wherein the first layer of the catheter tube defines an internal surface of the catheter tube.

11. The fecal drainage system of claim 10, wherein the third layer of the catheter tube that is intermediate the first layer and the second layer is the thickest layer of the catheter tube.

12. The fecal drainage system of claim 9, wherein the first layer and the second layer of the catheter tube comprise nylon 669.

13. The fecal drainage system of claim 9, wherein the first layer and the second layer of the catheter tube comprise nylon 669 blended with a reactive rubber.

14. The fecal drainage system of claim 13, wherein the nylon 669 blended with a reactive rubber further comprises one or more lubricants.

15. The fecal drainage system of claim 9, wherein the collection bag has one or more walls having odor barrier properties.

16. A fecal drainage system comprising:
   a collection bag having one or more walls with odor barrier properties; and
   a catheter tube connectable to the collection bag, the catheter tube having a plurality of layers, at least one of the plurality of layers including an odor barrier material comprising nylon 669, and at least one of the other layers including a material selected from the group consisting of thermoplastic elastomer (TPE), ethylene methyl acrylate film (EMA), thermoplastic polyurethane (TPU), styrene-butadiene copolymer (SBC), thermoplastic vulcanisate (TPV), and ethylene propylene diene monomer (EPDM).

17. The fecal drainage system of claim 16, wherein the nylon 669 is blended with a reactive rubber.

18. The fecal drainage system of claim 17, wherein the nylon 669 blended with a reactive rubber further comprises one or more lubricants.

* * * * *